United States Patent
Shaheen et al.

(10) Patent No.: US 8,007,819 B2
(45) Date of Patent: Aug. 30, 2011

(54) METHODS FOR DEACTIVATING ALLERGENS AND PREVENTING DISEASE

(75) Inventors: Elias Shaheen, Pleasanton, CA (US); Steven Bromberg, Pleasanton, CA (US); Vicki Friedman, Pleasanton, CA (US); Jennifer Fung-Sepulveda, Pleasanton, CA (US); Jennifer J. Julian, Pleasanton, CA (US)

(73) Assignee: The Clorox Company, Oakland, CA (US)

( * ) Notice: Subject to any disclaimer, the term of this patent is extended or adjusted under 35 U.S.C. 154(b) by 210 days.

(21) Appl. No.: 12/407,489

(22) Filed: Mar. 19, 2009

(65) Prior Publication Data

US 2009/0175958 A1    Jul. 9, 2009

Related U.S. Application Data

(63) Continuation of application No. 10/806,522, filed on Mar. 23, 2004, now Pat. No. 7,527,783.

(51) Int. Cl.
*A01N 25/00* (2006.01)

(52) U.S. Cl. ........ 424/405; 424/1.65; 424/1.85; 424/9.1; 424/9.2; 510/382

(58) Field of Classification Search .............. 221/26, 221/33, 36, 38, 47, 48, 50, 51, 62, 63, 303; 221/307–310; 424/1.11, 1.61, 1.65, 1.81, 424/1.85, 1.89, 9.1, 9.2, 400, 405; 510/108, 510/382
See application file for complete search history.

(56) References Cited

U.S. PATENT DOCUMENTS

| | | | |
|---|---|---|---|
| 3,749,772 A | 7/1973 | Cardarelli et al. | |
| 5,281,280 A | 1/1994 | Lisowski et al. | |
| 6,126,810 A | 10/2000 | Fricker et al. | |
| 6,296,744 B1 | 10/2001 | Djeiranishvili et al. | |
| 6,426,066 B1 | 7/2002 | Najafi et al. | |
| 6,428,801 B1 | 8/2002 | Suh et al. | |
| 6,528,214 B1 | 3/2003 | Pliner et al. | |
| 6,589,588 B1 | 7/2003 | Wester et al. | |
| 6,623,695 B2 | 9/2003 | Malchesky et al. | |
| 6,632,347 B1 | 10/2003 | Buckley et al. | |
| 7,527,783 B2 * | 5/2009 | Shaheen et al. | 424/9.2 |
| 2001/0022273 A1 | 9/2001 | Popov et al. | |
| 2001/0048097 A1 | 12/2001 | Inui et al. | |
| 2002/0040055 A1 | 4/2002 | Inui et al. | |
| 2002/0179884 A1 | 12/2002 | Hoshino et al. | |
| 2002/0182262 A1 | 12/2002 | Selkon | |
| 2003/0185704 A1 | 10/2003 | Bernard et al. | |
| 2003/0216271 A1 | 11/2003 | Scheper et al. | |
| 2004/0007251 A1 | 1/2004 | Koening et al. | |
| 2006/0177521 A1 * | 8/2006 | Bromberg et al. | 424/661 |

FOREIGN PATENT DOCUMENTS

| | | |
|---|---|---|
| EP | 1219323 | 7/2002 |
| EP | 1224955 | 7/2002 |
| WO | WO0001429 | 1/2000 |
| WO | WO 01/13962 | 3/2001 |
| WO | WO 01/20988 | 3/2001 |
| WO | WO 02/28187 | 4/2002 |

OTHER PUBLICATIONS

Hostynek et al. (Contact Dermatitis, 1990, vol. 23, pp. 316-324).
Shapas, Smith and Dickson, "Tactics for Reducing Indoor Arthropod Allergens," presented at the International Conference on urban Pests, Prague, Czech Republic, Jul. 1999.
Matsui et al., "Allergic Potentency of Recombinant Fel d 1 is reduced by low concentrations of chlorine bleach," J. Allergy and Clinical Immunology, 2003; 111:396-401.
Rutala et al., "Stability and Bactericidal Acitivty of Chlorine Solutions," Infection Control and Hospital Epidemiology, 1998, vol. 19, No. 5, 323-327.

* cited by examiner

*Primary Examiner* — D. L. Jones
(74) *Attorney, Agent, or Firm* — Alok Goel; Stacy H. Combs

(57) ABSTRACT

This invention relates to articles of manufacture containing liquid compositions of hypohalous acid or hypohalous acid salt for deactivating allergens and preventing diseases on hard surfaces, soft surfaces and in the air. The articles of manufacture contain usage instructions with health claims. This invention also includes methods of instructing the public and promoting the use of these compositions.

2 Claims, No Drawings

METHODS FOR DEACTIVATING ALLERGENS AND PREVENTING DISEASE

CROSS REFERENCE TO RELATED APPLICATION

The present application is a continuation of Co-pending application Ser. No. 10/806,522, which was filed Mar. 23, 2004, entitled "Methods for deactivating allergens and preventing disease", and incorporated herein.

BACKGROUND OF THE INVENTION

1. Field of the Invention

This invention relates to hypohalous acid and hypohalous acid salt, and compositions for deactivating allergens on hard surfaces, soft surfaces and in the air. The compositions are also useful for disinfecting, sanitizing, controlling odor, and controlling mold. The compositions can be used as is, diluted, dissolved, or mixed from a multi-component system. The compositions can support claims for a healthier environment and as a means to prevent illness. The compositions can be applied by a variety of means, including vaporizing, spraying, soaking, and applying by means of an impregnated substrate.

2. Description of the Related Art

A major concern associated with exposure to biological pollutants is allergic reactions, which range from rhinitis, nasal congestion, conjunctival inflammation, and urticaria to asthma. Notable triggers for these diseases are allergens derived from house dust mites; arthropods, including cockroaches; pets (cats, dogs, birds, rodents); molds; pollen; and protein-containing furnishings, including feathers, kapok, etc.

Molds are usually not a problem indoors, unless mold spores land on a wet or damp spot and begin growing. Molds have the potential to cause health problems. Molds produce allergens (substances that can cause allergic reactions), irritants, and in some cases, potentially toxic substances (mycotoxins). Inhaling or touching mold or mold spores may cause allergic reactions in sensitive individuals. Allergic responses include hay fever-type symptoms, such as sneezing, runny nose, red eyes, and skin rash (dermatitis). Allergic reactions to mold are common. They can be immediate or delayed. Molds can also cause asthma attacks in people with asthma who are allergic to mold. In addition, mold exposure can irritate the eyes, skin, nose, throat, and lungs of both mold-allergic and non-allergic people. Molds can also produce organic toxins. These toxins include Aflatoxin B, Citrinin, Cyclosporin A, Deoxynivalenol, Emodin, Gliotoxin, Griseofulvin, Ochratoxin A, Patulin, Roridin A, Satratoxin H, Sterigmatocystin, T-2 toxin, Verrucarin A, and Endotoxins.

Generally, acaricides are used for controlling house dust mites. However, house dust mites, such as *Dermatophagoides farinae, Dermatophagoides pteronyssinus*, and so on can be the source of allergens even after dying and these dead bodies of house dust mites gradually decompose and release fine particles of allergens. As a result, controlling of house dust mites by applying acaricides is not always useful to remove allergens from the environment.

Treatments which modify the protein allergens from dust mites may be successful it preventing an allergic response. One measure of the success of these treatments is an in-vitro ELISA test which measures the binding of the modified proteins to enzyme-bound monoclonal antibodies. This test can show reduced binding which may or may not indicate a changed allergenic response. In-vivo test methods measure the allergenic response directly.

Dust mite allergens, pet urine, and pet dander are non-living and, in general, are simple proteins. Prior art examples were able to modify dust mite allergens and other similar proteins so that they no longer complex with specific antibodies used in an ELISA test. These systems may not, however, denature living mold and pollen allergens, which are more complex than simple protein allergens. Mold and pollen allergens are living organisms containing protein, lipids and carbohydrates. Thus, treatments, which are effective for dust mites, may not be effective for molds and pollen. Additionally, prior art systems did not demonstrate the ability to modify the treated allergens so that they no longer generate any allergic response in animal systems.

U.S. 2002/0040055 to Inui et al. and U.S. 2001/0048097 to Inui et al. disclose a method to modify binding of mite and pollen allergens above 90% efficiency using the ELISA method by treatment with rare earth metal salt in alcohol and other solvents for 5 hours. European Patent Applications 1,224,955 and 1,219,323 to Reckitt Benckiser disclose deactivants for dust mite feces. These include 6-isopropyl-m-cresol and a list of essential oils, organic compounds, and inorganic compounds. These deactivants were tested on household dust treated for 4 hours and then tested for binding response in an ELISA test for dust mite allergens. In general, the deactivants were not as effective as the control, tannic acid. They also revealed significant amounts of active allergens remaining for both tannic acid and the disclosed deactivants. PCT Application WO00/01429 to Hughes et al. discloses a device generating spray droplets with a unipolar charge from a composition containing allergen deactivants. The air particles remaining after treatment were tested under ELISA conditions for binding. Since the charged droplet device spraying of any composition would be expected to reduce airborne particles, the effect of the particular composition used is unclear. In addition, presumably many allergenic airborne particles remained. PCT Application WO01/013962 to Houlbrook discloses steam to denature substantially more allergens than would be denatured under normal laundry conditions. No data on the test method or effectiveness is disclosed.

WO02/28187 to Hasan et al. discloses that certain metal ions can reduce dust mite allergen binding up to 82% by an ELISA test after treatment for 1 hour. U.S. Pat. No. 6,428,801 to Suh et al. discloses that various formulations can reduce dust mite populations after treatment for an undetermined time.

The use of a chemical or biocide that kills organisms such as mold is not recommended as a routine practice during mold cleanup. Dead mold may still cause allergic reactions in people, so it is not enough to simply kill the mold, it must also be removed.

Based on the prior art examples, various formulations have been discovered that will reduce dust mite or other allergens after extended treatment times. The need still exists for a simple treatment that will quickly kill and deactivate all types of allergens so that they will no longer generate an in-vivo allergic response.

SUMMARY OF THE INVENTION

In accordance with the above objects and those that will be mentioned and will become apparent below, one aspect of the present invention is an article of manufacture comprising:

a. a container enclosing a liquid composition;

b. a set of instructions; and c. a liquid composition comprising an allergen deactivating agent selected from the group consisting of a hypohalous acid, a hypohalous acid salt, and a combination thereof;

d. wherein said set of instructions comprises instructions to contact targets selected from the group consisting of hard surfaces, soft surfaces, and air with said liquid composition in its neat or diluted form to accomplish a result selected from the group consisting of, to prevent allergic response, to prevent illness, and a combination thereof.

In accordance with the above objects and those that will be mentioned and will become apparent below, another aspect of the present invention comprises a method of instructing the public by providing to the public a set of instructions for the use of an article of manufacture comprising:

a. a container, and b. a liquid composition comprising an allergen deactivating agent selected from the group consisting of a hypohalous acid, a hypohalous acid salt, and a combination thereof;

c. wherein said set of instructions comprises instructions to contact targets selected from the group consisting of hard surfaces, soft surfaces, and air with said liquid composition in its neat or diluted form to accomplish a result selected from the group consisting of, to prevent allergic response, to prevent illness, and a combination thereof.

In accordance with the above objects and those that will be mentioned and will become apparent below, another aspect of the present invention comprises a method of promoting the use of a liquid composition comprising an allergen deactivating agent selected from a group consisting of a hypohalous acid, a hypohalous acid salt, and a combination thereof: the method comprising the steps of;

a. informing the public to treat targets selected from a group consisting of hard surfaces, soft surfaces, air, and a combination thereof, and b. informing the public that said treatment of said targets with said liquid composition accomplishes a result selected from the group consisting of, preventing allergic response, preventing illness, and a combination thereof.

In accordance with the above objects and those that will be mentioned and will become apparent below, another aspect of the present invention comprises an in vivo test method for testing allergic response in animals, wherein said test method comprises the subcutaneous injection of allergens treated with a composition selected from a group consisting of a hypohalous acid, a hypohalous acid salt, and a combination thereof.

Further features and advantages of the present invention will become apparent to those of ordinary skill in the art in view of the detailed description of preferred embodiments below.

DETAILED DESCRIPTION

Before describing the present invention in detail, it is to be understood that this invention is not limited to particularly exemplified systems or process parameters that may, of course, vary. It is also to be understood that the terminology used herein is for the purpose of describing particular embodiments of the invention only, and is not intended to limit the scope of the invention in any manner.

All publications, patents and patent applications cited herein, whether supra or infra, are hereby incorporated by reference in their entirety to the same extent as if each individual publication, patent or patent application was specifically and individually indicated to be incorporated by reference.

It must be noted that, as used in this specification and the appended claims, the singular forms "a," "an" and "the" include plural referents unless the content clearly dictates otherwise. Thus, for example, reference to a "surfactant" includes two or more such surfactants.

Unless defined otherwise, all technical and scientific terms used herein have the same meaning as commonly understood by one of ordinary skill in the art to which the invention pertains. Although a number of methods and materials similar or equivalent to those described herein can be used in the practice of the present invention, the preferred materials and methods are described herein.

In the application, effective amounts are generally those amounts listed as the ranges or levels of ingredients in the descriptions, which follow hereto. Unless otherwise stated, amounts listed in percentage ("%'s") are in weight percent (based on 100% active) of the cleaning composition alone, not accounting for the substrate weight. Each of the noted cleaner composition components and substrates is discussed in detail below.

As used herein, the term "substrate" is intended to include any web, which is used to clean an article or a surface. Examples of cleaning sheets include, but are not limited to, mitts, webs of material containing a single sheet of material which is used to clean a surface by hand or a sheet of material which can be attached to a cleaning implement, such as a floor mop, handle, or a hand held cleaning tool, such as a toilet cleaning device.

As used herein, "wiping" refers to any shearing action that the substrate undergoes while in contact with a target surface. This includes hand or body motion, substrate-implement motion over a surface, or any perturbation of the substrate via energy sources such as ultrasound, mechanical vibration, electromagnetism, and so forth.

The term "cleaning composition", as used herein, is meant to mean and include a cleaning formulation having at least one surfactant.

The term "surfactant", as used herein, is meant to mean and include a substance or compound that reduces surface tension when dissolved in water or water solutions, or that reduces interfacial tension between two liquids, or between a liquid and a solid. The term "surfactant" thus includes anionic, nonionic and/or amphoteric agents.

Hypohalous Acid and Salts

Suitable hypohalous acids and salts may be provided by a variety of sources, including compositions that lead to the formation of positive halide ions and/or hypohalite ions, as well as compositions that are organic based sources of halides, such as chloroisocyanurates, haloamines, haloimines, haloimides and haloamides, or mixtures thereof. These compositions may also produce hypohalous acid or hypohalite species in situ. Suitable hypohalous acids and salts for use herein include the alkali metal and alkaline earth metal hypochlorites, hypobromites, hypoiodites, chlorinated trisodium phosphate dodecahydrates, potassium and sodium dichloroisocyanurates, potassium and sodium trichlorocyanurates, N-chloroimides, N-chloroamides, N-chlorosulfamide, N-chloroamines, chlorohydantoins such as dichlorodimethyl hydantoin and chlorobromo dimethylhydantoin, bromo-compounds corresponding to the chloro-compounds above, and compositions which generate the corresponding hypohalous acids, or mixtures thereof.

In one embodiment wherein the compositions herein are liquid, said hypohalite compositions is an alkali metal and/or alkaline earth metal hypochlorite, or mixtures thereof. Compositions may be an alkali metal and/or alkaline earth metal hypochlorite selected from the group consisting of sodium hypochlorite, potassium hypochlorite, magnesium hypochlorite, lithium hypochlorite and calcium hypochlorite, and mixtures thereof.

The hypohalous acids and salt composition may be an equilibrium mixture of hypochlorous acid and sodium hypochlorite. The active species is present in an amount from above zero to about 15 weight percent of the composition, or from about 0.001 weight percent (10 ppm) to about 10 weight percent of the composition, or from about 0.005 (50 ppm) to about 5 weight percent of the composition.

The amount of available halogen oxidant in the composition is determined by placing samples of the composition into about 50 milliliters of distilled water, followed by addition of about 10 milliliters of a 10 weight/weight percent solution of potassium iodide and addition of about 10 milliliters of a 10 volume percent solution of sulfuric acid, the resulting mixture being well stirred. The resulting yellow to brown solution, whose color is the result of oxidation of free iodine ion ($I^-$) to molecular iodine ($I_2$), was then volumetrically titrated to an essentially colorless endpoint by addition of standardized 0.1 Molar sodium thiosulfate ($Na_2S_2O_3$) titrant. Calculation then expresses the result as percent of available molecular chlorine ($Cl_2$), that is to say assigning two equivalents per mole of titrated hypohalite oxidant. Stability results are then expressed by repeated assays over time using identically prepared samples resulting from the same composition, normalized to 100 percent representative of the starting available chlorine measured initially.

During the course of evaluating various oxidants and antimicrobials for their allergen deactivating ability, we have found that a very dilute solution (on the order of 40-80 ppm) of primarily hypochlorous acid can effectively deactivate allergens. Presumably the low levels of oxidant are still able to break up the allergen proteins, rendering them biologically inert.

While still extremely effective, the low concentration and nearly neutral pH (6.9) of hypochlorous virtually eliminates surface damage. There is no sticky residue that can affect the feel of fabrics and there may be minimal dye damage. The solution may be aerosolized to treat air directly, or applied to surfaces.

Aerosols are known to have a low collision rate between denaturant and allergen particles. As a result, the denaturant must be used in high concentrations to be effective. Using this approach with conventional denaturants, which may be irritating or fragranced at high levels, can cause health problems.

Nonwoven Substrate

In one embodiment, the substrate of the present invention is composed of nonwoven fibers or paper. The term nonwoven is to be defined according to the commonly known definition provided by the "Nonwoven Fabrics Handbook" published by the Association of the Nonwoven Fabric Industry.

Methods of making nonwovens are well known in the art. Generally, these nonwovens can be made by air-laying, water-laying, meltblowing, coforming, spunbonding, or carding processes in which the fibers or filaments are first cut to desired lengths from long strands, passed into a water or air stream, and then deposited onto a screen through which the fiber-laden air or water is passed. The air-laying process is described in U.S. Pat. App. 2003/0036741 to Abba et al. and U.S. Pat. App. 2003/0118825 to Melius et al. The resulting layer, regardless of its method of production or composition, is then subjected to at least one of several types of bonding operations to anchor the individual fibers together to form a self-sustaining substrate. In the present invention the nonwoven substrate can be prepared by a variety of processes including, but not limited to, air-entanglement, hydroentanglement, thermal bonding, and combinations of these processes.

In one aspect, dry cleaning substrates can be provided with dry or substantially dry cleaning or disinfecting agents coated on or in the multicomponent, multilobal fiber layer. In addition, the cleaning substrates can be provided in a pre-moistened and/or saturated condition. The wet cleaning substrates can be maintained over time in a sealable container such as, for example, within a bucket with an attachable lid, sealable plastic pouches or bags, canisters, jars, tubs and so forth. Desirably the wet, stacked cleaning substrates are maintained in a resealable container. The use of a resealable container is particularly desirable when using volatile liquid compositions since substantial amounts of liquid can evaporate while using the first substrates thereby leaving the remaining substrates with little or no liquid. Exemplary resealable containers and dispensers include, but are not limited to, those described in U.S. Pat. No. 4,171,047 to Doyle et al., U.S. Pat. No. 4,353,480 to McFadyen, U.S. Pat. No. 4,778,048 to Kaspar et al., U.S. Pat. No. 4,741,944 to Jackson et al., U.S. Pat. No. 5,595,786 to McBride et al.; the entire contents of each of the aforesaid references are incorporated herein by reference. The cleaning substrates can be incorporated or oriented in the container as desired and/or folded as desired in order to improve ease of use or removal as is known in the art. The cleaning substrates of the present invention can be provided in a kit form, wherein a plurality of cleaning substrates and a cleaning tool are provided in a single package.

Surfactants

The composition of the invention may contain surfactants. The surfactants should be stable to hypohalous acid or hypohalous acid salt if long term storage is desired. If the solutions of the composition are generated prior to use, then surfactants having less stability may be used. Examples of surfactants having relatively good stability can be found in U.S. Pat. Nos. 6,413,925 and 5,851,421.

The composition may contain one or more surfactants selected from anionic, nonionic, cationic, ampholytic, amphoteric and zwitterionic surfactants and mixtures thereof. A typical listing of anionic, nonionic, ampholytic, and zwitterionic classes, and species of these surfactants, is given in U.S. Pat. No. 3,929,678 to Laughlin and Heuring. A list of suitable cationic surfactants is given in U.S. Pat. No. 4,259,217 to Murphy. Where present, ampholytic, amphotenic and zwitteronic surfactants are generally used in combination with one or more anionic and/or nonionic surfactants. The surfactants may be present at a level of from about 0% to 90%, or from about 0.001% to 50%, or from about 0.01% to 25% by weight.

The composition may comprise an anionic surfactant. Essentially any anionic surfactants useful for detersive purposes can be comprised in the cleaning composition. These can include salts (including, for example, sodium, potassium, ammonium, and substituted ammonium salts such as mono-, di- and tri-ethanolamine salts) of the anionic sulfate, sulfonate, carboxylate and sarcosinate surfactants. Anionic surfactants may comprise a sulfonate or a sulfate surfactant. Anionic surfactants may comprise an alkyl sulfate, a linear or branched alkyl benzene sulfonate, or an alkyldiphenyloxide disulfonate, as described herein.

Other anionic surfactants include the isethionates such as the acyl isethionates, N-acyl taurates, fatty acid amides of methyl tauride, alkyl succinates and sulfosuccinates, monoesters of sulfosuccinate (for instance, saturated and unsaturated C 12-C18 monoesters) diesters of sulfosuccinate (for instance saturated and unsaturated C6-C14 diesters), N-acyl sarcosinates. Resin acids and hydrogenated resin acids are also suitable, such as rosin, hydrogenated rosin, and resin acids and hydrogenated resin acids present in or derived from tallow oil. Anionic sulfate surfactants suitable for use herein include the linear and branched primary and secondary alkyl sulfates, alkyl ethoxysulfates, fatty oleoyl glycerol sulfates, alkyl phenol ethylene oxide ether sulfates, the C5-C17acyl-N—(C1-C4 alkyl) and —N—(C1-C2 hydroxyalkyl) glucamine sulfates, and sulfates of alkylpolysacchanides such as the sulfates of alkylpolyglucoside (the nonionic nonsulfated compounds being described herein). Alkyl sulfate surfactants may be selected from the linear and branched primary C10-C18 alkyl sulfates, the C11-C15 branched chain alkyl sulfates, or the C12-C14 linear chain alkyl sulfates.

Alkyl ethoxysulfate surfactants may be selected from the group consisting of the C10-C18 alkyl sulfates which have been ethoxylated with from 0.5 to 20 moles of ethylene oxide per molecule. The alkyl ethoxysulfate surfactant may be a C11-C18, or a C11-C15 alkyl sulfate which has been ethoxylated with from 0.5 to 7, or from 1 to 5, moles of ethylene oxide per molecule. One aspect of the invention employs mixtures of the alkyl sulfate and/or sulfonate and alkyl ethoxysulfate surfactants. Such mixtures have been disclosed in PCT Patent Application No. WO 93/18124.

Anionic sulfonate surfactants suitable for use herein include the salts of C5-C20 linear alkylbenzene sulfonates, alkyl ester sulfonates, C6-C22 primary or secondary alkane sulfonates, C6-C24 olefin sulfonates, sulfonated polycarboxylic acids, alkyl glycerol sulfonates, fatty acyl glycerol sulfonates, fatty oleyl glycerol sulfonates, and any mixtures thereof. Suitable anionic carboxylate surfactants include the alkyl ethoxy carboxylates, the alkyl polyethoxy polycarboxylate surfactants and the soaps ('alkyl carboxyls'), especially certain secondary soaps as described herein. Suitable alkyl ethoxy carboxylates include those with the formula RO(CH$_2$CH$_2$O)$_x$CH$_2$COO$^-$M$^+$ wherein R is a C6 to C18 alkyl group, x ranges from 0 to 10, and the ethoxylate distribution is such that, on a weight basis, the amount of material where x is 0 is less than 20% and M is a cation. Suitable alkyl polyethoxypolycarboxylate surfactants include those having the formula RO—(CHR$^1$—CHR$^2$-0)-R$^3$ wherein R is a C6 to C18 alkyl group, x is from 1 to 25, R$^1$ and R$^2$ are selected from the group consisting of hydrogen, methyl acid radical, succinic acid radical, hydroxysuccinic acid radical, and mixtures thereof, and R$^3$ is selected from the group consisting of hydrogen, substituted or unsubstituted hydrocarbon having between 1 and 8 carbon atoms, and mixtures thereof.

Suitable soap surfactants include the secondary soap surfactants, which contain a carboxyl unit connected to a secondary carbon. Suitable secondary soap surfactants for use herein are water-soluble members selected from the group consisting of the water-soluble salts of 2-methyl-1-undecanoic acid, 2-ethyl-1-decanoic acid, 2-propyl-1-nonanoic acid, 2-butyl-1-octanoic acid and 2-pentyl-1-heptanoic acid. Certain soaps may also be included as suds suppressors.

Other suitable anionic surfactants are the alkali metal sarcosinates of formula R—CON(R$^1$)CH—)COOM, wherein R is a C5-C17 linear or branched alkyl or alkenyl group, R$^1$ is a C1-C4 alkyl group and M is an alkali metal ion. Examples are the myristyl and oleoyl methyl sarcosinates in the form of their sodium salts.

Essentially any alkoxylated nonionic surfactants are suitable herein, for instance, ethoxylated and propoxylated nonionic surfactants. Alkoxylated surfactants can be selected from the classes of the nonionic condensates of alkyl phenols, nonionic ethoxylated alcohols, nonionic ethoxylated/propoxylated fatty alcohols, nonionic ethoxylate/propoxylate condensates with propylene glycol, and the nonionic ethoxylate condensation products with propylene oxide/ethylene diamine adducts.

The condensation products of aliphatic alcohols with from 1 to 25 moles of alkylene oxide, particularly ethylene oxide and/or propylene oxide, are suitable for use herein. The alkyl chain of the aliphatic alcohol can either be straight or branched, primary or secondary, and generally contains from 6 to 22 carbon atoms. Also suitable are the condensation products of alcohols having an alkyl group containing from 8 to 20 carbon atoms with from 2 to 10 moles of ethylene oxide per mole of alcohol.

Polyhydroxy fatty acid amides suitable for use herein are those having the structural formula R$^2$CONR$^1$Z wherein: R$^1$ is H, C1-C4 hydrocarbyl, 2-hydroxyethyl, 2-hydroxypropyl, ethoxy, propoxy, or a mixture thereof, for instance, C1-C4 alkyl, or C1 or C2 alkyl; and R$^2$ is a C5-C31 hydrocarbyl, for instance, straight-chain C5-C19 alkyl or alkenyl, or straight-chain C9-C17 alkyl or alkenyl, or straight-chain C11-C17 alkyl or alkenyl, or mixture thereof-, and Z is a polyhydroxyhydrocarbyl having a linear hydrocarbyl chain with at least 3 hydroxyls directly connected to the chain, or an alkoxylated derivative (for example, ethoxylated or propoxylated) thereof. Z may be derived from a reducing sugar in a reductive amination reaction, for example, when Z is a glycityl.

Suitable fatty acid amide surfactants include those having the formula: R$^1$CON(R$^2$)$_2$ wherein R$^1$ is an alkyl group containing from 7 to 21, or from 9 to 17 carbon atoms and each R$^2$ is selected from the group consisting of hydrogen, C1-C4 alkyl, C1-C4 hydroxyalkyl, and —(C$_2$H$_4$O)$_x$H, where x is in the range of from 1 to 3.

Suitable alkylpolysaccharides for use herein are disclosed in U.S. Pat. No. 4,565,647 to Llenado, having a hydrophobic group containing from 6 to 30 carbon atoms and a polysaccharide, e.g., a polyglycoside, hydrophilic group containing from 1.3 to 10 saccharide units. Alkylpolyglycosides may have the formula: R$^2$O(C$_n$H$_{2n}$O)$_t$(glycosyl)$_x$ wherein R$^2$ is selected from the group consisting of alkyl, alkylphenyl, hydroxyalkyl, hydroxyalkylphenyl, and mixtures thereof in which the alkyl groups contain from 10 to 18 carbon atoms; n is 2 or 3; t is from 0 to 10, and x is from 1.3 to 8. The glycosyl may be derived from glucose.

Suitable amphoteric surfactants for use herein include the amine oxide surfactants and the alkyl amphocarboxylic acids. Suitable amine oxides include those compounds having the formula R$^3$(OR$^4$)$_x$NO(R$^5$)$_2$ wherein R$^3$ is selected from an alkyl, hydroxyalkyl, acylamidopropyl and alkylphenyl group, or mixtures thereof, containing from 8 to 26 carbon atoms; R$^4$ is an alkylene or hydroxyalkylene group containing from 2 to 3 carbon atoms, or mixtures thereof, x is from 0 to 5, preferably from 0 to 3; and each R$^5$ is an alkyl or hydroxyalkyl group containing from 1 to 3, or a polyethylene oxide group containing from 1 to 3 ethylene oxide groups. Suitable amine oxides are C10-C18 alkyl dimethylamine oxide, and C10-18 acylamido alkyl dimethylamine oxide. A suitable example of an alkyl amphodicarboxylic acid is Miranol™ C2M Conc. manufactured by Miranol, Inc., Dayton, N.J.

Zwitterionic surfactants can also be incorporated into the cleaning compositions. These surfactants can be broadly described as derivatives of secondary and tertiary amines, derivatives of heterocyclic secondary and tertiary amines, or derivatives of quaternary ammonium, quaternary phosphonium or tertiary sulfonium compounds. Betaine and sultaine surfactants are exemplary zwitterionic surfactants for use herein.

Suitable betaines are those compounds having the formula $R(R^1)_2N^+R^2COO^-$ wherein R is a C6-C18 hydrocarbyl. group, each $R^1$ is typically C1-C3 alkyl, and $R^2$ is a C1-C5 hydrocarbyl group. Suitable betaines are C12-18 dimethyl-ammonio hexanoate and the C10-18 acylamidopropane (or ethane) dimethyl (or diethyl) betaines. Complex betaine surfactants are also suitable for use herein.

Suitable cationic surfactants to be used herein include the quaternary ammonium surfactants. The quaternary ammonium surfactant may be a mono C6-C16, or a C6-C10 N-alkyl or alkenyl ammonium surfactant wherein the remaining N positions are substituted by methyl, hydroxyethyl or hydroxypropyl groups. Suitable are also the mono-alkoxylated and bis-alkoxylated amine surfactants.

Another suitable group of cationic surfactants, which can be used in the cleaning compositions, are cationic ester surfactants. The cationic ester surfactant is a compound having surfactant properties comprising at least one ester (i.e. —COO—) linkage and at least one cationically charged group. Suitable cationic ester surfactants, including choline ester surfactants, have for example been disclosed in U.S. Pat. Nos. 4,228,042, 4,239,660 and 4,260,529. The ester linkage and cationically charged group may be separated from each other in the surfactant molecule by a spacer group consisting of a chain comprising at least three atoms (i.e. of three atoms chain length), or from three to eight atoms, or from three to five atoms, or three atoms. The atoms forming the spacer group chain are selected from the group consisting, of carbon, nitrogen and oxygen atoms and any mixtures thereof, with the proviso that any nitrogen or oxygen atom in said chain connects only with carbon atoms in the chain. Thus spacer groups having, for example, —O—O— (i.e. peroxide), —N—N—, and —N—O— linkages are excluded, whilst spacer groups having, for example —CH$_2$—O—, CH$_2$— and —CH$_2$—NH—CH$_2$— linkages are included. The spacer group chain may comprise only carbon atoms, or the chain is a hydrocarbyl chain.

The composition may comprise cationic mono-alkoxylated amine surfactants, for instance, of the general formula: $R^1R^2R^3N^+ApR^4X^-$ wherein $R^1$ is an alkyl or alkenyl moiety containing from about 6 to about 18 carbon atoms, or from 6 to about 16 carbon atoms, or from about 6 to about 14 carbon atoms; $R^2$ and $R^3$ are each independently alkyl groups containing from one to about three carbon atoms, for instance, methyl, for instance, both $R^2$ and $R^3$ are methyl groups; $R^4$ is selected from hydrogen, methyl and ethyl; $X^-$ is an anion such as chloride, bromide, methylsulfate, sulfate, or the like, to provide electrical neutrality; A is a alkoxy group, especially a ethoxy, propoxy or butoxy group; and p is from 0 to about 30, or from 2 to about 15, or from 2 to about 8. The $ApR^4$ group in the formula may have p=1 and is a hydroxyalkyl group, having no greater than 6 carbon atoms whereby the —OH group is separated from the quaternary ammonium nitrogen atom by no more than 3 carbon atoms. Suitable $ApR^4$ groups are —CH$_2$CH$_2$—OH, —CH$_2$CH$_2$CH$_2$-0H, —CH$_2$CH (CH$_3$)—OH and —CH(CH$_3$)CH$_2$—OH. Suitable $R^1$ groups are linear alkyl groups, for instance, linear $R^1$ groups having from 8 to 14 carbon atoms.

Suitable cationic mono-alkoxylated amine surfactants for use herein are of the formula $R^1(CH_3)(CH_3)N^+$ (CH$_2$CH$_2$O)$_{2-5}$H X$^-$ wherein $R^1$ is C10-C18 hydrocarbyl and mixtures thereof, especially C10-C14 alkyl, or C10 and C12 alkyl, and X is any convenient anion to provide charge balance, for instance, chloride or bromide.

As noted, compounds of the foregoing type include those wherein the ethoxy (CH$_2$CH$_2$O) units (EO) are replaced by butoxy, isopropoxy [CH(CH$_3$)CH$_2$O] and [CH$_2$CH(CH$_3$)O] units (i-Pr) or n-propoxy units (Pr), or mixtures of EO and/or Pr and/or i-Pr units.

The cationic bis-alkoxylated amine surfactant may have the general formula: $R^1R^2N^+ApR^3A'qR^4X^-$ wherein $R^1$ is an alkyl or alkenyl moiety containing from about 8 to about 18 carbon atoms, or from 10 to about 16 carbon atoms, or from about 10 to about 14 carbon atoms; $R^2$ is an alkyl group containing from one to three carbon atoms, for instance, methyl; $R^3$ and $R^4$ can vary independently and are selected from hydrogen, methyl and ethyl, $X^-$ is an anion such as chloride, bromide, methylsulfate, sulfate, or the like, sufficient to provide electrical neutrality. A and A' can vary independently and are each selected from C1-C4 alkoxy, for instance, ethoxy, (i.e., —CH$_2$CH$_2$O—), propoxy, butoxy and mixtures thereof, p is from 1 to about 30, or from 1 to about 4 and q is from 1 to about 30, or from 1 to about 4, or both p and q are 1.

Suitable cationic bis-alkoxylated amine surfactants for use herein are of the formula $R^1CH_3N^+(CH_2CH_2OH)$ (CH$_2$CH$_2$OH)X$^-$, wherein $R^1$ is C10-C18 hydrocarbyl and mixtures thereof, or C10, C12, C14 alkyl and mixtures thereof, $X^-$ is any convenient anion to provide charge balance, for example, chloride. With reference to the general cationic bis-alkoxylated amine structure noted above, since in one example compound $R^1$ is derived from (coconut) C12-C14 alkyl fraction fatty acids, $R^2$ is methyl and $ApR^3$ and $A'qR^4$ are each monoethoxy.

Other cationic bis-alkoxylated amine surfactants useful herein include compounds of the formula: $R^1R^2N^+$—(CH$_2$CH$_2$O)$_p$H—(CH$_2$CH$_2$O)$_q$H X$^-$ wherein $R^1$ is C10-C18 hydrocarbyl, or C10-C14 alkyl, independently p is 1 to about 3 and q is 1 to about 3, $R^2$ is C1-C3 alkyl, for example, methyl, and $X^-$ is an anion, for example, chloride or bromide.

Other compounds of the foregoing type include those wherein the ethoxy (CH$_2$CH$_2$O) units (EO) are replaced by butoxy (Bu) isopropoxy [CH(CH$_3$)CH$_2$O] and [CH$_2$CH (CH$_3$)O] units (i-Pr) or n-propoxy units (Pr), or mixtures of EO and/or Pr and/or i-Pr units.

The inventive compositions may include at least one fluorosurfactant selected from nonionic fluorosurfactants, cationic fluorosurfactants, and mixtures thereof which are soluble or dispersible in the aqueous compositions being taught herein, sometimes compositions which do not include further detersive surfactants, or further organic solvents, or both. Suitable nonionic fluorosurfactant compounds are found among the materials presently commercially marketed under the tradename Fluorad® (ex. 3M Corp.) Exemplary fluorosurfactants include those sold as Fluorad® FC-740, generally described to be fluorinated alkyl esters; Fluorad® FC-430, generally described to be fluorinated alkyl esters; Fluorad® FC-431, generally described to be fluorinated alkyl esters; and, Fluorad® FC-170-C, which is generally described as being fluorinated alkyl polyoxyethlene ethanols.

Suitable nonionic fluorosurfactant compounds include those which is believed to conform to the following formulation: $C_nF_{2n+1}SO_2N(C_2H_5)(CH_2CH_2O)_xCH_3$ wherein: n has a value of from 1-12, or from 4-12, or 8; x has a value of from 4-18, or from 4-10, or 7; which is described to be a nonionic fluorinated alkyl alkoxylate and which is sold as Fluorad® FC-171 (ex. 3M Corp., formerly Minnesota Mining and Manufacturing Co.).

Additionally suitable nonionic fluorosurfactant compounds are also found among the materials marketed under the tradename ZONYL® (DuPont Performance Chemicals). These include, for example, ZONYL® FSO and ZONYL® FSN. These compounds have the following formula: $RfCH_2CH_2O(CH_2CH_2O)_xH$ where Rf is $F(CF_2CF_2)_y$. For ZONYL® FSO, x is 0 to about 15 and y is 1 to about 7. For ZONYL® FSN, x is 0 to about 25 and y is 1 to about 9.

An example of a suitable cationic fluorosurfactant compound has the following structure: $C_nF_{2n+1}SO_2NHC_3H_6N^+(CH_3)_3I^-$ where n~8. This cationic fluorosurfactant is available under the tradename Fluorad® FC-135 from 3M. Another example of a suitable cationic fluorosurfactant is $F_3—(CF_2)_n—(CH_2)_mSCH_2CHOH—CH_2—N^+R_1R_2R_3Cl^-$ wherein: n is 5-9 and m is 2, and $R_1$, $R_2$ and $R_3$ are —$CH_3$. This cationic fluorosurfactant is available under the tradename ZONYL® FSD (available from DuPont, described as 2-hydroxy-3-((gamma-omega-perfluoro-$C_{6-20}$-alkyl)thio)-N,N,N-trimethyl-1-propyl ammonium chloride). Other cationic fluorosurfactants suitable for use in the present invention are also described in EP 866,115 to Leach and Niwata.

The fluorosurfactant selected from the group of nonionic fluorosurfactant, cationic fluorosurfactant, and mixtures thereof may be present in amounts of from 0.001 to 5% wt., preferably from 0.01 to 1% wt., and more preferably from 0.01 to 0.5% wt.

Solvent

The composition of the invention may contain solvents. The solvents should be stable to hypohalous acid or hypohalous acid salt if long term storage is desired. If the solutions of the composition are generated prior to use, then solvents having less stability may be used.

Suitable organic solvents include, but are not limited to, $C_{1-6}$ alkanols, $C_{1-6}$ diols, $C_{1-10}$ alkyl ethers of alkylene glycols, $C_{3-24}$ alkylene glycol ethers, polyalkylene glycols, short chain carboxylic acids, short chain esters, isoparafinic hydrocarbons, mineral spirits, alkylaromatics, terpenes, terpene derivatives, terpenoids, terpenoid derivatives, formaldehyde, and pyrrolidones. Alkanols include, but are not limited to, methanol, ethanol, n-propanol, isopropanol, butanol, pentanol, and hexanol, and isomers thereof. Diols include, but are not limited to, methylene, ethylene, propylene and butylene glycols. Alkylene glycol ethers include, but are not limited to, ethylene glycol monopropyl ether, ethylene glycol monobutyl ether, ethylene glycol monohexyl ether, diethylene glycol monopropyl ether, diethylene glycol monobutyl ether, diethylene glycol monohexyl ether, propylene glycol methyl ether, propylene glycol ethyl ether, propylene glycol n-propyl ether, propylene glycol monobutyl ether, propylene glycol t-butyl ether, di- or tri-polypropylene glycol methyl or ethyl or propyl or butyl ether, acetate and propionate esters of glycol ethers. Short chain carboxylic acids include, but are not limited to, acetic acid, glycolic acid, lactic acid and propionic acid. Short chain esters include, but are not limited to, glycol acetate, and cyclic or linear volatile methylsiloxanes. Water insoluble solvents such as isoparafinic hydrocarbons, mineral spirits, alkylaromatics, terpenoids, terpenoid derivatives, terpenes, and terpenes derivatives can be mixed with a water-soluble solvent when employed.

Examples of organic solvent having a vapor pressure less than 0.1 mm Hg (20° C.) include, but are not limited to, dipropylene glycol n-propyl ether, dipropylene glycol t-butyl ether, dipropylene glycol n-butyl ether, tripropylene glycol methyl ether, tripropylene glycol n-butyl ether, diethylene glycol propyl ether, diethylene glycol butyl ether, dipropylene glycol methyl ether acetate, diethylene glycol ethyl ether acetate, and diethylene glycol butyl ether acetate (all available from ARCO Chemical Company).

The solvents can be present at a level of from 0.001% to 10%, or from 0.01% to 10%, or from 1% to 4% by weight.

Additional Adjuncts

The compositions optionally contain one or more of the following adjuncts: stain and soil repellants, lubricants, odor control agents, perfumes, fragrances and fragrance release agents, brighteners, and fluorescent whitening agents. Other adjuncts include, but are not limited to, acids, electrolytes, dyes and/or colorants, solubilizing materials, stabilizers, thickeners, defoamers, hydrotropes, cloud point modifiers, preservatives, and other polymers. The solubilizing materials, when used, include, but are not limited to, hydrotropes (e.g. water soluble salts of low molecular weight organic acids such as the sodium and/or potassium salts of toluene, cumene, and xylene sulfonic acid). The acids, when used, include, but are not limited to, mineral acids, organic hydroxy acids, citric acids, keto acid, and the like. Electrolytes, when used, include, calcium, sodium and potassium chloride. Thickeners, when used, include, but are not limited to, polyacrylic acid, xanthan gum, calcium carbonate, aluminum oxide, alginates, guar gum, methyl, ethyl, clays, and/or propyl hydroxycelluloses. Defoamers, when used, include, but are not limited to, silicones, aminosilicones, silicone blends, and/or silicone/hydrocarbon blends.

Preservatives, when used, include, but are not limited to, mildewstat or bacteriostat, methyl, ethyl and propyl parabens, short chain organic acids (e.g. acetic, lactic and/or glycolic acids), bisguanidine compounds (e.g. Dantagard and/or Glydant) and/or short chain alcohols (e.g. ethanol and/or IPA). The mildewstat or bacteriostat includes, but is not limited to, mildewstats (including non-isothiazolone compounds) including Kathon GC, a 5-chloro-2-methyl-4-isothiazolin-3-one, KATHON ICP, a 2-methyl-4-isothiazolin-3-one, and a blend thereof, and KATHON 886, a 5-chloro-2-methyl-4-isothiazolin-3-one, all available from Rohm and Haas Company; BRONOPOL, a 2-bromo-2-nitropropane 1,3 diol, from Boots Company Ltd., PROXEL CRL, a propyl-p-hydroxybenzoate, from ICI PLC; NIPASOL M, an o-phenyl-phenol, $Na^+$ salt, from Nipa Laboratories Ltd., DOWICIDE A, a 1,2-Benzoisothiazolin-3-one, from Dow Chemical Co., and IRGASAN DP 200, a 2,4,4'-trichloro-2-hydroxydiphenylether, from Ciba-Geigy A.G.

Antimicrobial Agent

The composition of the invention may contain antimicrobial agents. The antimicrobial agents should be stable to hypohalous acid or hypohalous acid salt if long term storage is desired. If the solutions of the composition are generated prior to use, then antimicrobial agents having less stability may be used.

Antimicrobial agents include quaternary ammonium compounds and phenolics. Non-limiting examples of these quaternary compounds include benzalkonium chlorides and/or substituted benzalkonium chlorides, di($C_6$-$C_{14}$)alkyl di short chain ($C_{1-4}$ alkyl and/or hydroxyalkl) quaternaryammonium salts, N-(3-chloroallyl) hexaminium chlorides, benzethonium chloride, methylbenzethonium chloride, and cetylpyridinium chloride. Other quaternary compounds include the group consisting of dialkyldimethyl ammonium chlorides, alkyl dimethylbenzylammonium chlorides, dialkylmethylbenzylammonium chlorides, and mixtures thereof. Biguanide antimicrobial actives including, but not limited to polyhexamethylene biguanide hydrochloride, p-chlorophenyl biguanide; 4-chlorobenzhydryl biguanide, halogenated hexidine such as, but not limited to, chlorhexidine (1,1'-hexamethylene-bis-5-(4-chlorophenyl biguanide) and its salts are also in this class.

Builder/Buffer

The composition of the invention may contain a builder or buffer. The builder or buffer should be stable to hypohalous acid or hypohalous acid salt if long term storage is desired. If the solutions of the composition are generated prior to use, then builders or buffers having less stability may be used.

The composition may include a builder or buffer, which can be used as a pH adjusting agent or as a sequestering agent in the composition. A variety of builders or buffers can be used and they include, but are not limited to, phosphate-silicate compounds, carbon dioxide or carbonate, zeolites, alkali metal, ammonium and substituted ammonium polyacetates, trialkali salts of nitrilotriacetic acid, carboxylates, polycarboxylates, carbonates, bicarbonates, polyphosphates, aminopolycarboxylates, polyhydroxysulfonates, and starch derivatives.

Builders or buffers can also include polyacetates and polycarboxylates. The polyacetate and polycarboxylate compounds include, but are not limited to, sodium, potassium, lithium, ammonium, and substituted ammonium salts of ethylenediamine tetraacetic acid, ethylenediamine triacetic acid, ethylenediamine tetrapropionic acid, diethylenetriamine pentaacetic acid, nitrilotriacetic acid, oxydisuccinic acid, iminodisuccinic acid, mellitic acid, polyacrylic acid or polymethacrylic acid and copolymers, benzene polycarboxylic acids, gluconic acid, sulfamic acid, oxalic acid, phosphoric acid, phosphonic acid, organic phosphonic acids, acetic acid, and citric acid. These builders or buffers can also exist either partially or totally in the hydrogen ion form.

The builder agent can include sodium and/or potassium salts of EDTA and substituted ammonium salts. The substituted ammonium salts include, but are not limited to, ammonium salts of methylamine, dimethylamine, butylamine, butylenediamine, propylamine, triethylamine, trimethylamine, monoethanolamine, diethanolamine, triethanolamine, isopropanolamine, ethylenediamine tetraacetic acid and propanolamine.

Buffering and pH adjusting agents, when used, include, but are not limited to, organic acids, mineral acids, alkali metal and alkaline earth salts of silicate, metasilicate, polysilicate, borate, hydroxide, carbonate, carbamate, phosphate, polyphosphate, pyrophosphates, triphosphates, tetraphosphates, ammonia, hydroxide, monoethanolamine, monopropanolamine, diethanolamine, dipropanolamine, triethanolamine, and 2-amino-2-methylpropanol. Preferred buffering agents for compositions of this invention are nitrogen-containing materials. Some examples are amino acids such as lysine or lower alcohol amines like mono-, di-, and tri-ethanolamine. Other preferred nitrogen-containing buffering agents are tri(hydroxymethyl)amino methane (TRIS), 2-amino-2-ethyl-1,3-propanediol, 2-amino-2-methyl-propanol, 2-amino-2-methyl-1,3-propanol, disodium glutamate, N-methyl diethanolamide, 2-dimethylamino-2-methylpropanol (DMAMP), 1,3-bis(methylamine)-cyclohexane, 1,3-diamino-propanol N,N'-tetra-methyl-1,3-diamino-2-propanol, N,N-bis(2-hydroxyethyl)glycine (bicine) and N-tris(hydroxymethyl)methyl glycine (tricine). Other suitable buffers include ammonium carbamate, citric acid, acetic acid. Mixtures of any of the above are also acceptable. Useful inorganic buffers/alkalinity sources include ammonia, the alkali metal carbonates and alkali metal phosphates, e.g., sodium carbonate, sodium polyphosphate. For additional buffers see WO 95/07971, which is incorporated herein by reference. Other preferred pH adjusting agents include sodium or potassium hydroxide.

When employed, the builder, buffer, or pH adjusting agent comprises at least about 0.001% and typically about 0.01-5% of the cleaning composition. Preferably, the builder or buffer content is about 0.01-2%.

Substances Generally Recognized as Safe

Compositions according to the invention may comprise substances generally recognized as safe (GRAS), including essential oils, oleoresins (solvent-free) and natural extractives (including distillates), and synthetic flavoring materials and adjuvants. Compositions may also comprise GRAS materials commonly found in cotton, cotton textiles, paper and paperboard stock dry food packaging materials (referred herein as substrates) that have been found to migrate to dry food and, by inference may migrate into the inventive compositions when these packaging materials are used as substrates for the inventive compositions.

The composition of the invention may contain GRAS materials. The GRAS materials should be stable to hypohalous acid or hypohalous acid salt if long term storage is desired. If the solutions of the composition are generated prior to use, then GRAS materials having less stability may be used.

Suitable GRAS materials are listed in the Code of Federal Regulations (CFR) Title 21 of the United States Food and Drug Administration, Department of Health and Human Services, Parts 180.20, 180.40 and 180.50, which are hereby incorporated by reference. These suitable GRAS materials include essential oils, oleoresins (solvent-free), and natural extractives (including distillates). The GRAS materials may be present in the compositions in amounts of up to about 10% by weight, preferably in amounts of 0.01 and 5% by weight.

Suitable GRAS materials include oils and oleoresins (solvent-free) and natural extractives (including distillates) derived from alfalfa, allspice, almond bitter (free from prussic acid), ambergris, ambrette seed, *angelica, angostura* (cusparia bark), anise, apricot kernel (persic oil), asafetida, balm (lemon balm), balsam (of Peru), basil, bay leave, bay (myrcia oil), bergamot (bergamot orange), bois de rose (*Aniba rosaeodora* Ducke), cacao, camomile (chamomile) flowers, *cananga, capsicum*, caraway, cardamom seed (cardamon), carob bean, carrot, cascarilla bark, *cassia* bark, Castoreum, celery seed, cheery (wild bark), chervil, cinnamon bark, Civet (zibeth, zibet, zibetum), ceylon (*Cinnamomum zeylanicum* Nees), cinnamon (bark and leaf), citronella, citrus peels, clary (clary sage), clover, coca (decocainized), coffee, cognac oil (white and green), cola nut (kola nut), coriander, cumin (cummin), curacao orange peel, *cusparia* bark, dandelion, dog grass (quackgrass, *triticum*), elder flowers, estragole (esdragol, esdragon, estragon, tarragon), fennel (sweet), fenugreek, galanga (galangal), *geranium*, ginger, grapefruit, guava, hickory bark, horehound (hoarhound), hops, horsemint, hyssop, immortelle (*Helichrysum augustifolium* DC), jasmine, juniper (berries), laurel berry and leaf, lavender, lemon, lemon grass, lemon peel, lime, linden flowers, locust bean, lupulin, mace, mandarin (*Citrus reticulata* Blanco), marjoram, mate, menthol (including menthyl acetate), molasses (extract), musk (Tonquin musk), mustard, naringin, neroli (bigarade), nutmeg, onion, orange (bitter, flowers, leaf, flowers, peel), *origanum*, palmarosa, paprika, parsley, peach kernel (persic oil, pepper (black, white), peanut (stearine), peppermint, Peruvian balsam, petitgrain lemon, petitgrain mandarin (or tangerine), *pimenta, pimenta* leaf, pipsissewa leaves, pomegranate, prickly ash bark, quince seed, rose (absolute, attar, buds, flowers, fruit, hip, leaf), rose geranium, rosemary, saffron, sage, St. John's bread, savory, *schinus molle* (*Schinus molle* L), sloe berries, spearmint, spike lavender, tamarind, tangerine, tarragon, tea (*Thea sinensis* L.), thyme, tuberose, turmeric, vanilla, violet (flowers, leaves), wild cherry bark, ylang-ylang and zedoary bark.

Suitable synthetic flavoring substances and adjuvants are listed in the Code of Federal Regulations (CFR) Title 21 of the United States Food and Drug Administration, Department of Health and Human Services, Part 180.60, which is hereby incorporated by reference. These GRAS materials may be present in the compositions in amounts of up to about 1% by weight, preferably in amounts of 0.01 and 0.5% by weight.

Suitable synthetic flavoring substances and adjuvants that are generally recognized as safe for their intended use, include acetaldehyde (ethanal), acetoin (acetyl methylcarbinol), anethole (parapropenyl anisole), benzaldehyde (benzoic aldehyde), n-Butyric acid (butanoic acid), d- or l-carvone (carvol), cinnamaldehyde (cinnamic aldehyde), citral (2,6-dimethyloctadien-2,6-al-8, gera-nial, neral), decanal (N-decylaldehyde, capraldehyde, capric aldehyde, caprinaldehyde, aldehyde C-10), ethyl acetate, ethyl butyrate, 3-Methyl-3-phenyl glycidic acid ethyl ester (ethyl-methyl-phenyl-glycidate, so-called strawberry aldehyde, C-16 aldehyde), ethyl vanillin, geraniol (3,7-dimethyl-2,6 and 3,6-octadien-1-ol), geranyl acetate (geraniol acetate), limonene (d-, l-, and dl-), linalool (linalol, 3,7-dimethyl-1,6-octadien-3-ol), linalyl acetate (bergamol), methyl anthranilate (methyl-2-aminobenzoate), piperonal (3,4-methylenedioxy-benzaldehyde, heliotropin) and vanillin.

Suitable GRAS substances that may be present in the inventive compositions that have been identified as possibly migrating to food from cotton, cotton textiles, paper and paperboard materials used in dry food packaging materials are listed in the Code of Federal Regulations (CFR) Title 21 of the United States Food and Drug Administration, Department of Health and Human Services, Parts 180.70 and 180.90, which are hereby incorporated by reference. The GRAS materials may be present in the compositions either by addition or incidentally owing to migration from the substrates to the compositions employed in the invention, or present owing to both mechanisms. If present, the GRAS materials may be present in the compositions in amounts of up to about 1% by weight.

Suitable GRAS materials that are suitable for use in the invention, identified as originating from either cotton or cotton textile materials used as substrates in the invention, include beef tallow, carboxymethylcellulose, coconut oil (refined), cornstarch, gelatin, lard, lard oil, oleic acid, peanut oil, potato starch, sodium acetate, sodium chloride, sodium silicate, sodium tripolyphosphate, soybean oil (hydrogenated), talc, tallow (hydrogenated), tallow flakes, tapioca starch, tetrasodium pyrophosphate, wheat starch and zinc chloride.

Suitable GRAS materials that are suitable for use in the invention, identified as originating from either paper or paperboard stock materials used as substrates in the invention, include alum (double sulfate of aluminum and ammonium potassium, or sodium), aluminum hydroxide, aluminum oleate, aluminum palmitate, casein, cellulose acetate, cornstarch, diatomaceous earth filler, ethyl cellulose, ethyl vanillin, glycerin, oleic acid, potassium sorbate, silicon dioxides, sodium aluminate, sodium chloride, sodium hexametaphosphate, sodium hydrosulfite, sodium phosphoaluminate, sodium silicate, sodium sorbate, sodium tripolyphosphate, sorbitol, soy protein (isolated), starch (acid modified, pregelatinized and unmodified), talc, vanillin, zinc hydrosulfite and zinc sulfate.

Fragrance

The composition of the invention may contain fragrance. The fragrance should be stable to hypohalous acid or hypohalous acid salt if long term storage is desired. If the solutions of the composition are generated prior to use, then fragrances having less stability may be used.

Compositions of the present invention may comprise from about 0.001% to about 5% by weight of the fragrance. Compositions of the present invention may comprise from about 0.005% to about 2.5% by weight of the fragrance. Compositions of the present invention may comprise from about 0.01% to about 1% by weight of the fragrance.

As used herein the term "fragrance" relates to the mixture of perfume raw materials that are used to impart an overall pleasant odor profile to a composition. As used herein the term "perfume raw material" relates to any chemical compound which is odiferous when in an un-entrapped state, for example in the case of pro-perfumes, the perfume component is considered, for the purposes of this invention, to be a perfume raw material, and the pro-chemistry anchor is considered to be the entrapment material. In addition "perfume raw materials" are defined by materials with a ClogP value preferably greater than about 0.1, more preferably greater than about 0.5, even more preferably greater than about 1.0. As used herein the term "ClogP" means the logarithm to base 10 of the octanol/water partition coefficient. This can be readily calculated from a program called "CLOGP" which is available from Daylight Chemical Information Systems Inc., Irvine Calif., U.S.A. Octanol/water partition coefficients are described in more detail in U.S. Pat. No. 5,578,563.

The individual perfume raw materials which comprise a known natural oil can be found by reference to Journals commonly used by those skilled in the art such as "Perfume and Flavourist" or "Journal of Essential Oil Research". In addition some perfume raw materials are supplied by the fragrance houses as mixtures in the form of proprietary specialty accords. In order that fragrance oils can be developed with the appropriate character for the present invention the perfume raw materials have been classified based upon two key physical characteristics:

(i) boiling point (BP) measured at 1 atmosphere pressure. The boiling point of many fragrance materials are given in Perfume and Flavor Chemicals (Aroma Chemicals), Steffen Arctander (1969). Perfume raw materials for use in the present invention are divided into volatile raw materials (which have a boiling point of less than, or equal to, about 250° C.) and residual raw materials (which have a boiling point of greater than about 250° C., preferably greater than about 275° C.). All perfume raw materials will preferably have boiling points (BP) of about 500° C. or lower.

(ii) odor detection threshold which is defined as the lowest vapour concentration of that material which can be olfactorily detected. The odor detection threshold and some odor detection threshold values are discussed in e.g., "Standardized Human Olfactory Thresholds", M. Devos et al, IRL Press at Oxford University Press, 1990, and "Compilation of Odor and Taste Threshold Values Data", F. A. Fazzalar, editor ASTM Data Series DS 48A, American Society for Testing and Materials, 1978, both of said publications being incorporated by reference. Perfume raw materials for use in the present invention can be classified as those with a low odor detection threshold of less than 50 parts per billion, preferably less than 10 parts per billion and those with a high odor detection threshold which are detectable at greater than 50 parts per billion (values as determined from the reference above).

Since, in general, perfume raw materials refer to a single individual compound, their physical properties (such ClogP, boiling point, odor detection threshold) can be found by referencing the texts cited above. In the case that the perfume raw material is a natural oil, which comprises a mixture of several compounds, the physical properties of the complete oil should be taken as the weighted average of the individual components. In the case that the perfume raw material is a proprietary specialty accord the physical properties should be obtain from the Supplier.

In general a broad range of suitable perfume raw materials can be found in U.S. Pat. Nos. 4,145,184, 4,209,417, 4,515, 705, and 4,152,272. Non-limiting examples of perfume raw materials which are useful for blending to formulate fragrances for the present invention are given below. Any perfume raw materials, natural oils or proprietary specialty accords known to a person skilled in the art can be used within the present invention.

Volatile perfume raw materials useful in the present invention are selected from, but are not limited to, aldehydes with a relative molecular mass of less than or equal to about 200, esters with a relative molecular mass of less than or equal to about 225, terpenes with a relative molecular mass of less than or equal to about 200, alcohols with a relative molecular mass of less than or equal to about 200 ketones with a relative molecular mass of less than or equal to about 200, nitriles, pyrazines, and mixtures thereof.

Examples of volatile perfume raw materials having a boiling point of less than, or equal to, 250° C., with a low odor detection are selected from, but are not limited to, anethol, methyl heptine carbonate, ethyl aceto acetate, para cymene, nerol, decyl aldehyde, para cresol, methyl phenyl carbinyl acetate, ionone alpha, ionone beta, undecylenic aldehyde, undecyl aldehyde, 2,6-nonadienal, nonyl aldehyde, octyl aldehyde. Further examples of volatile perfume raw materials having a boiling point of less than, or equal to, 250° C., which are generally known to have a low odour detection threshold include, but are not limited to, phenyl acetaldehyde, anisic aldehyde, benzyl acetone, ethyl-2-methyl butyrate, damascenone, damascone alpha, damascone beta, flor acetate, frutene, fructone, herbavert, iso cyclo citral, methyl isobutenyl tetrahydro pyran, iso propyl quinoline, 2,6-nonadien-1-ol, 2-methoxy-3-(2-methylpropyl)-pyrazine, methyl octine carbonate, tridecene-2-nitrile, allyl amyl glycolate, cyclogalbanate, cyclal C, melonal, gamma nonalactone, cis 1,3-oxathiane-2-methyl-4-propyl.

Other volatile perfume raw materials having a boiling point of less than, or equal to, 250° C., which are useful in the present invention, which have a high odor detection threshold, are selected from, but are not limited to, benzaldehyde, benzyl acetate, camphor, carvone, borneol, bornyl acetate, decyl alcohol, eucalyptol, linalool, hexyl acetate, iso-amyl acetate, thymol, carvacrol, limonene, menthol, iso-amyl alcohol, phenyl ethyl alcohol, alpha pinene, alpha terpineol, citronellol, alpha thujone, benzyl alcohol, beta gamma hexenol, dimethyl benzyl carbinol, phenyl ethyl dimethyl carbinol, adoxal, allyl cyclohexane propionate, beta pinene, citral, citronellyl acetate, citronellal nitrile, dihydro myrcenol, geraniol, geranyl acetate, geranyl nitrile, hydroquinone dimethyl ether, hydroxycitronellal, linalyl acetate, phenyl acetaldehyde dimethyl acetal, phenyl propyl alcohol, prenyl acetate, triplal, tetrahydrolinalool, verdox, cis-3-hexenyl acetate.

Examples of residual "middle and base note" perfume raw materials having a boiling point of greater than 250° C., which have a low odor detection threshold are selected from, but are not limited to, ethyl methyl phenyl glycidate, ethyl vanillin, heliotropin, indol, methyl anthranilate, vanillin, amyl salicylate, coumarin. Further examples of residual perfume raw materials having a boiling point of greater than 250° C. which are generally known to have a low odor detection threshold include, but are not limited to, ambrox, bacdanol, benzyl salicylate, butyl anthranilate, cetalox, ebanol, cis-3-hexenyl salicylate, lilial, gamma undecalactone, gamma dodecalactone, gamma decalactone, calone, cymal, dihydro iso jasmonate, iso eugenol, lyral, methyl beta naphthyl ketone, beta naphthol methyl ether, para hydroxyl phenyl butanone, 8-cyclohexadecen-1-one, oxocyclohexadecen-2-one/habanolide, florhydral, intreleven aldehyde.

Other residual "middle and base note" perfume raw materials having a boiling point of greater than 250° C. which are useful in the present invention, but which have a high odor detection threshold, are selected from, but are not limited to, eugenol, amyl cinnamic aldehyde, hexyl cinnamic aldehyde, hexyl salicylate, methyl dihydro jasmonate, sandalore, veloutone, undecavertol, exaltolide/cyclopentadecanolide, zingerone, methyl cedrylone, sandela, dimethyl benzyl carbinyl butyrate, dimethyl benzyl carbinyl isobutyrate, triethyl citrate, cashmeran, phenoxy ethyl isobutyrate, iso eugenol acetate, helional, iso E super, ionone gamma methyl, pentalide, galaxolide, phenoxy ethyl propionate.

Water and pH

The water should be present at a level of less than about 99.999%. The water may be deionized, filtered to remove impurities including metals and organic carbon, purified by reverse osmosis, purified by distillation, or any combination thereof. During preparation there may be a need for hygiene and segregation to prevent the introduction of compounds that are oxidized by hypochlorite since these become more important at low concentrations where the loss of a few ppm may be significant.

The composition may be adjusted for pH using a pH adjusting agent. Suitable pH adjusting agents include carbon dioxide, alkali metal carbonate, alkali metal bicarbonate, alkali metal silicates, alkali metal hydroxide, alkali phosphate salt, alkaline earth phosphate salt, alkali borate salt, hydrochloric acid, nitric acid, sulfuric acid, alkali metal hydrogen sulfate, acetic acid, other carboxylic acids, polycarboxylates, organic sulfonic acids, sulfamic acid, amine, alkyl amine, dialkyl amine, and trialkyl amine. The composition may have a pH from 1 to 13. The composition may have a pH from 2 to 12. The composition may have a pH from 2 to 5. The composition may have a pH from 5 to 8. The composition may have a pH from 6 to 8. The composition may have a pH from 6 to 7.5. The composition may have a pH from 9 to 13. The composition may have a pH from 10 to 12.

Method of Use

The composition may be dispersed into the air. The composition may be dispersed using an atomizer, a vaporizer, a nebulizer, or a spray device. The composition may be delivered on a continuous basis, such as with a humidifier. The composition may be delivered on a pulsed basis, such as with a canister on a timer. One spray device is an electrostatic sprayer, as described in WO0120988. The composition may be applied to skin surfaces. The composition may be delivered from a variety of containers, such as a dual chambered bottle, a trigger spray bottle, an aerosol canister, and a bleach pen.

The composition may be stored or shipped in a variety of containers, including glass, ABS, polycarbonate, high density polyethylene, low density polyethylene, high density polypropylene, low density polypropylene, polyethylene terephthalate, or polyvinylchloride. A variety of additives may affect the stability of the composition. For instance, the density of the polyethylene resin may be modified by copolymerizing with a small amount of a short chain alkylene, e.g., butene, hexene or octene. Various other additives can be added, such as colorants, UV blockers, opacifying agents, and antioxidants, such as hindered phenols, e.g., BHT, Irganox 1010 (Ciba-Geigy A.G.), Irganox 1076 (Ciba-Geigy A.G.), Ionol (Shell Chemical Co.). Mold release agents and plasticizers can be added, especially to other types of plastics. The containers may have barrier films to increase storage stability. Suitable barrier films may include nylons, polyethylene terephthalate, fluorinated polyethylenes, and Barex (a copolymer of acrylonitrile and methylmethacrylate that is available from British Petroleum).

The composition may be applied to soft surfaces including clothing, bedding, upholstery, curtains, and carpets. The composition may be applied to soft surfaces by spraying, by wiping, by direct application, by immersion, or as part of the laundry washing process.

The composition may be applied to hard surfaces including kitchen surfaces, bathroom surfaces, walls, floors, outdoor surfaces, automobiles, countertops, food contact surfaces, toys, food products including fruits and vegetables. The composition may be applied to hard surfaces by spraying, by wiping, by direct application, by immersion, or as part of the normal cleaning process.

The composition may be applied on human and animal surfaces, including external skin areas and internal cavities. The composition may have lower skin sensitivity and may be appropriate to be taken orally or by inhalation. The composition may be applied to human and animal surfaces by spraying, by wiping, by direct application, by immersion, or as part of the normal treatment process. The composition may be applied as a thickened gel. The composition may be applied using a device to direct its application, such as a bleach pen. The composition may be applied as a wound dressing.

The composition may be applied with a nonwoven substrate, wipe or cleaning pad on inanimate, household surfaces, including floors, counter tops, furniture, windows, walls, and automobiles. The composition may be applied to baby and children's items, including toys, bottles, pacifiers, etc. The composition may be applied with a nonwoven substrate, wipe or cleaning pad on human and animal surfaces, including external skin areas and internal cavities. Other surfaces include stainless steel, chrome, and shower enclosures. The nonwoven substrate, wipe or cleaning pad can be packaged individually or together in canisters, tubs, etc. The nonwoven substrate, wipe or cleaning pad can be used with the hand, or as part of a cleaning implement attached to a tool or motorized tool, such as one having a handle. Examples of tools using a nonwoven substrate, wipe or pad include U.S. Pat. No. 6,611,986 to Seals, WO00/71012 to Belt et al., U.S. Pat. App. 2002/0129835 to Pieroni and Foley, and WO00/27271 to Policicchio et al.

For certain uses, for example, for human and animal surfaces, the composition may be thickened. The composition may be thickened using surfactant thickening, polymer thickening, or other means. Thickening may allow more controlled application or application from a device. Examples of thickened and unthickened compositions can be found in U.S. Pat. Nos. 6,162,371, 6,066,614, 6,153,120, 6,037,318, 6,313,082, 5,688,435, 6,413,925, 6,297,209, 6,100,228, 5,916,859, 5,851,421, 5,688,756, 5,767,055, 5,055,219, and 5,075,029.

The anodic oxidation of chloride in an electrolysis cell results in the production of a number of oxychlorine ions including hypochlorite, chlorite, chlorate, and perchlorate. Chlorite is readily oxidized to chlorate. Perchlorate may be an undesirable contaminant in the environment due to its low reactivity, high mobility, and inhibition of thyroid function. The production of hypochlorite via chlorination of caustic water is not believed to result in the formation of perchlorate. This route may be advantageous for certain uses where minor amounts of perchlorate would be undesirable.

The composition may be prepared by mixing a solid composition with water. The solid composition may be a tablet, granular composition, paste, or other solid composition. The composition may be prepared by diluting a liquid composition with water. The water may be purified. The composition may be prepared by mixing two liquids, for example, from a dual chambered container or a dual chambered spray bottle.

The compositions of the invention can be diluted prior to use with tap water or water of higher purity. Preparation of dilute compositions for storage, for example as pre-diluted in bottles, may require water of higher purity. This higher purity water can be obtained by a variety of processes, including for example, distillation, filtering, sodium cation exchange (soft water), hydrogen cation exchange (deionized water without anion exchange), reverse osmosis, activated carbon treatment, ultrafiltration, nanofiltration, electrodialysis, and UV light treatment.

The compositions of the invention can be diluted prior to use from a concentrated liquid or solid composition. For instance, liquid sodium hypochlorite optionally containing surfactants or other additives of 5.25% available chlorine concentration can be diluted to below 500 ppm available chlorine concentration. Tablets or powders having solid hypochlorite or hypochlorite generators can be dissolved in water to deliver compositions below 500 ppm concentration. Examples of compositions that can be diluted are described in U.S. Pat. Nos. 6,297,209, 6,100,228, 5,851,421, 5,688,756, 5,376,297, 5,034,150, 6,534,465, 6,503,877, 6,416,687, 6,180,583, and 6,051,676.

The compositions of the invention can be delivered as part of a multi-compartment delivery system, for example as described in U.S. Pat. Nos. 5,954,213, 5,316,159, WO2004/014760, U.S. Pat. Nos. 6,610,254, and 6,550,694.

The compositions of the invention can be used for a food rinse, for cleaning food-contact surfaces, and for toxicologically safe cleaning. This may involve the use of food-safe ingredients, GRAS ingredients, or ingredients with low toxicologically impact. Methods describing this use and possible compositions can be found in U.S. Pat. Nos. 6,455,086, 6,313,049, U.S. 2002/0132742, U.S. 2001/0014655, WO99/00025, and U.S. 2002/0151452.

The compositions of the invention can be used to sterilize medical instruments. Dilute hypochlorite will discolor or degrade tubing and other sensitive parts to less extent than concentrated hypochlorite. The compositions may be used in kidney dialysis machines or as an irrigating agent in endodontic treatment.

The compositions of the invention can be used in agricultural applications, for example, seed and seedling treatments, dormant sprays for fruit trees, stored grain treatments, dips or sprays for any post-harvest plant material and their containers, treatments for soil, either on the land or in containers, treatments for transportation and storage to market, treatments for transportation, storage, and display at market (retail or wholesale), treatments for import and export regulations, and treatments for preventing the accidental introduction of alien pest organisms. The compositions of the invention can be used for the meat, poultry, dairy, seafood, and aquaculture industries, for example, equipment treatments, living quarters treatments, dips or sprays for eggs and containers, dips or sprays for meat and containers, treatments for rendering operations, treatments for transportation and storage to market, treatments for transportation, storage, and display at market (retail or wholesale), treatments for import and export regulations, treatments for preventing alien pest organisms from crossing borders, treating disease on live animals (terrestrial or aquatic), including udder treatments, and dips or sprays for milking equipment, transfer lines, and containers. The compositions of the invention can be used for homeland security, for example, treatments for preventing the intentional introduction of alien pest organisms or deadly organisms.

The compositions of the invention can be used to preserve and maintain the freshness of freshly cut flowers and other cut plants. The compositions of the invention can be used to prevent the build-up of microorganisms that contribute to the decaying of stems and abscission and scenesing of leaves and flowers. The compositions of the invention can be used to preserve and extend the shelf life of freshly cut fruits and vegetables such as cut melon, cantaloupe, strawberry, potatoes, etc. The compositions of the invention can be used to eradicate hepatitis virus A from fresh strawberries and other fruits and vegetables. The compositions of the invention can be used for in the sprout industry to treat seeds of various plants including alfalfa, wheat, barely and all other edible plant to control the spread of food-borne diseases such as *Salmonella, E. coli, Campylobacter*, etc. The compositions of the invention can be used in washing and treating shoes that have been moldy. The compositions of the invention can be used with sponges, cheese-cloth, paper towel and other non-woven articles to clean and remove and kill mold, bacteria and viruses from soft and hard surfaces. The compositions of the invention can be used to control mold in school. The compositions of the invention can be used as a spray or wipe product. The compositions of the invention can be used to control the spread of germs on hard surfaces in school. The compositions of the invention can be used to control the spread of hepatitis among jails. The compositions of the invention can be used in laundry to kill germs. The compositions of the invention can be used in long-term care centers and public gyms, where, for example, they can be applied as a spray or wipe product on hard surfaces to kill all germs that are transmitted via environmental surfaces and human. The compositions of the invention can be used in laundry to disinfect towels, and other articles that carry germs. The compositions of the invention can be used for in public areas where, for example, they can be sprayed on a large scale in parks, streets, public places to control disease-causing agents such as SARS, calicivirus, enterovirus, FMD, and other viruses. The compositions of the invention can be used as wipes or spray to disinfect all environmental surfaces. The compositions of the invention can be used on ships and cruise ships where, for example, they can be used to control the spread if norwalk virus, calicivirus, and influenza virus. The compositions of the invention can be used to control cross contamination due to *Salmonella* and *Campylobacter*. The compositions of the invention can be used for to protect from biological warfare where, for example, they can be used to spray on humans, (i.e., army personals, medics, etc.) in case of potential presence of biological warfare agents such as Anthrax, BT, Sarin, Small Pox, and SARS, etc. The compositions of the invention can be used for disinfecting military vehicles, airplanes, and others. The compositions of the invention can be used to control the outbreak of Infectious agents where, for example, they can be used to disinfect airlines (inside and outside), trains, buses and all sort of transportation means to control the spread of pathogens. The compositions of the invention can be used for to disinfect shoes (via a wipe of dipping or spraying) at airports and other ports of entry. The compositions of the invention can be used to control insects where, for example, they can be used a spray to kill New Zealand Slug and other slugs or insects. The compositions of the invention can be used to kill fleas. The compositions of the invention can be used to control animal and insect pathogens where, for example, they can be used to control animal and bird viruses on hard surfaces and soft surfaces. Such viruses include SARS, bird flu virus, calicivirus, mad cow disease virus, parvovirus, feline viruses, etc. Also, they can be used to dip teats in to control various pathogens.

The composition may be part of an article of manufacture comprising: a container enclosing a liquid composition; a set of instructions; and a liquid composition comprising an allergen neutralizing agent selected from a group consisting of a hypohalous acid, a hypohalous acid salt, and a combination thereof, wherein said set of instructions comprises instructions to contact targets selected from a group consisting of hard surfaces, soft surfaces, or air with said liquid composition in its neat or diluted form to prevent allergic response, to prevent illness, or a combination thereof.

The composition may be part of an article of manufacture wherein said article of manufacture in addition to the usage instructions bears an additional indication comprising a term selected from the group consisting of: healthy, healthier, reduce the occurrence of illness, control the spread of illness in the home, protect your family from illness, keep your home healthier, keep your family well, break the cycle of illness in the home, reduce the risk of common illnesses, and combinations thereof.

The composition may be part of an article of manufacture, wherein said article of manufacture in addition to the usage instructions bears an additional indication comprising a term selected from the group consisting of: neutralizes mold allergens, denatures toxins from mold, neutralizes toxins from mold, neutralizes protein allergens, controls allergens, removes allergens by cleaning, removes allergens by wiping, removes allergens in the laundry, reduces respiratory illness, reduces hay fever, reduces absenteeism, denatures mold allergens, prevents allergenic reactions, prevents allergenic reaction in humans, prevents allergenic symptoms due to mold, kills mold, destroys mold spores, destroys mold spores that cause adverse health effects, proven to prevent mold-triggered allergic sensitization in humans, proven to prevent mold-triggered allergic sensitization in animals, reduces the risk of mold-triggered allergic sensitization, reduces the risk of mold-triggered allergic response, destroys mold spores that induce allergic symptoms, neutralizes mold specific antigens, and prevents non-immune inflammatory reactions to mold.

The composition may be part of an article of manufacture. The article of manufacture may include a set of instructions. The set of instructions may be used with a method of instructing the public by providing to the public a set of instructions for the use of an article of manufacture comprising a container and a liquid composition comprising an allergen neutralizing agent selected from a group consisting of a hypohalous acid, a hypohalous acid salt, and a combination thereof, wherein said set of instructions comprises instructions to contact targets selected from a group consisting of hard surfaces, soft surfaces, or air with said liquid composition in its neat or diluted form to prevent allergic response, to prevent illness, or a combination thereof. The instructions may relate to preventing the spread of illness with a liquid composition comprising a hypohalous acid salt composition. The method of instructing the public may include information that an allergic response represents a response to pollen, dust mite, or mold allergens. The set of instructions may be provided to the public via electronic and/or print media. The set of instructions may be posted at the point of sale adjacent the package. The set of instructions may be posted on a global computer network at an address associated with products from a group consisting of said liquid composition, said target surface, or a combination thereof.

The method of promoting the use of the liquid composition comprising an allergen neutralizing agent selected from a group consisting of a hypohalous acid, a hypohalous acid salt, and a combination thereof may include use instructions to prevent allergic response and/or illness, the method comprising the step of informing the public that the treatment of targets selected from a group consisting of hard surfaces, soft surfaces, or air with said composition reduces and/or prevents allergic response and/or illness. The method of promoting the use of the composition may include the step of informing the consumer via electronic and/or print media.

The use of the composition may include an in vivo test method for testing allergic response in animals, wherein said test method comprises the subcutaneous injection of allergens treated with a composition selected from a group consisting of a hypohalous acid, a hypohalous acid salt, and a combination thereof.

EXAMPLES

Table I shows that diluted hypochlorite solutions have good stability at near neutral pH, especially when diluted with water relatively free from metal ions and salts. The solutions also have good stability in the presence of chelants, such as pyrophosphate and orthophosphate. The initial concentration of the concentrated sodium hypochlorite was 6.448% sodium hypochlorite.

TABLE I

|  | Initial av. chlorine in ppm (pH) | Loss at 70° F. after 27 days | Loss at 120° F. after 27 days |
| --- | --- | --- | --- |
| Conc. Hypochlorite and tap water | 79 (pH 7.6) | 7% | 52% |
| Conc. Hypochlorite and distilled deionized water | 77 (pH 7.5) | 0% | 22% |
| Conc. Hypochlorite, 23 ppm Orthophosphate, distilled deionized water | 81 (pH 7.6) | 6% | 25% |
| Conc. Hypochlorite, 11.5 ppm Pyrophosphate, distilled deionized water | 80 (pH 7.6) | 4% | 29% |

Table II shows compositions of the invention with impurity concentrations. Low concentrations of these impurities can enhance the stability of the compositions. In some cases, the initial concentrations of the impurities may be higher and the impurities may be made less reactive or inert over time. In these cases, the compositions may have increased stability upon aging.

TABLE II

|  | Diluted hypochlorite | Diluted hypochlorite |
| --- | --- | --- |
| Available chlorine, ppm | 200 ppm | 40 ppm |
| pH | 7.9 | 5.1 |
| Copper | <100 ppb | <80 ppb |
| Nickel | <10 ppb | <8 ppb |
| Cobalt | <30 ppb | <20 ppb |
| Total organic carbon | <500 ppb | <200 ppb |

Table III shows that dust mite allergens are effectively denatured with diluted hypochlorite solutions down to 5 ppm available chlorine. The pH obtained for diluted hypochlorite solution at 4 ppm was 6.51. The compositions are also effective against allergens within 30 seconds.

Product efficacy screening was performed by using a modified antibody capture ELISA (where a recombinant antigen is coated onto polystyrene, the product is added directly to predetermined wells and incubated for a selected period of time, the results of the product treated wells are compared against those of untreated wells, the concentration is calculated against a standard curve). This method differs from the antigen capture ELISA in that product interference which affected antibody-antigen complex is not considered because the product is added directly to the antigen/allergen, the wells are washed of excess product and the labeled antibody is incubated onto the remains of the antigen. Protein fragmentation was revealed by SDS-PAGE method and loss of Allergenic activity (antibody binding to antigen) was observed in Western blot (immunoblot).

TABLE III

|  | Available chlorine, ppm | Dust mite allergen, % reduction |
| --- | --- | --- |
| Diluted hypochlorite | 0.77 | 75 |
|  | 4.0 | 98 |
|  | 7.8 | 99 |
|  | 19.4 | 100 |
|  | 38.4 | 100 |
|  | 57.7 | 100 |
|  | 77 | 100 (30 sec) |

Table IV shows that diluted hypochlorite is effective at sanitizing and disinfecting as measured by efficacy against *Staphylococcus aureus*. Tests were conducted using the AOAC Germicidal Spray Products test method (AOAC 961.02, 15th edition, SOP No. 001-057-06). An approximate 48-hour suspension of *Staphylococcus aureus* grown up in AOAC Synthetic Broth was used for testing. The culture concentration was adjusted to yield a target of $4 \times 10^4$ per slide once dried. For the runs to be conducted with organic soil load, a separate bacteria suspension was prepared with fetal bovine serum where the serum load was 5%. A volume of 0.01 ml was inoculated per glass slide. A sterile bent needle was used to spread the inoculum to within ⅛" from the edge. For each inoculation run, the slides were dried in the 35° C. incubator until completely dry. Prior to testing, bottle caps were replaced with trigger sprayers. The triggers were primed and testing was started by spraying the contaminated surfaces from 6-8 cm distance for 2-3 seconds. The surface was completely wet by about 3-4 full pumps. The amount of product that was dispensed per trigger ranged from 2.24 g to 2.90 g. For the samples that were pipeted onto the contaminated surfaces, the dispensing volume was between 2.5 ml per slide (with filter paper) and 5 ml per slide (without filter paper).

TABLE IV

| | Available chlorine in ppm | pH | Sample with residual bacteria |
|---|---|---|---|
| Diluted hypochlorite | 707.6 | 9.70 | 0/60 |
| Diluted hypochlorite After storage 120 F. for 1 month | 63.4 | 7.36 | 0/60 |

Table V shows that the compositions are effective at killing a variety of viruses and spores.

TABLE V

| | Diluted hypochlorite |
|---|---|
| Polio I Virus | Effective |
| Influenza A Virus | Effective |

The compositions are effective at controlling mold growth. Diluted hypochlorite tested against *penicillium* mold in a petri dish gave growth inhibition.

The dilute hypochlorite compositions are effective at controlling odors. Dilute hypochlorite can control odors by both killing the odor-causing bacterial as well as oxidizing the odor molecules themselves, breaking them down into smaller, odorless components. An initial test was done using garlic juice in small plastic containers. A drop of garlic juice was placed in each of two plastic containers at room temperature and allowed to equilibrate for 10 minutes. The containers are then opened and one is sprayed with dilute hypochlorite and one with plain water. The containers were then closed and again allowed to equilibrate for 10 minutes. Then a corner of the container is opened to smell the contents. The containers sprayed with dilute hypochlorite had less garlic odor than the one sprayed with water.

The compositions of the invention can give minimal fabric damage compared to other hypochlorite compositions. Cotton, rayon, and wool were sprayed with dilute hypochlorite until damp and allowed to dry between sprayings. Test was repeated for upwards of 20+ sprays. No visible damage was observed. Swatches of bleach sensitive blue-dyed cotton (Intralite Turquoise GL) were soaked in dilute hypochlorite solutions. Swatches showed no discoloration for several hours. Some bleaching was observed when soaked for longer times and was easily observable after 24 hours.

The composition of the invention was found to kill *Aspergillus fumigatus* Conidia spores in solution and to inactivate *Aspergillus fumigatus* Conidia antigen in solution. The composition was also tested on hard surfaces. The composition of the invention was found to reduce mold growth on drywall 6 logs compared to water (none). The composition of the invention was found to reduce mold growth on plywood 6 logs compared to water (none). The composition of the invention was found to reduce mold growth on oriented strand board more than 6 logs compared to water (none). The compositions of the invention were tested for in vivo allergic response in humans, wherein said test method comprises the subcutaneous injection of allergens treated with the composition. The residue after treatment on oriented strand board was evaluated by prick skin testing on test subjects who had a history of positive skin prick to *Aspergillus fumigatus*.

Results from the in vivo testing suggest that the inventive compositions will reduce or prevent respiratory ailments caused by allergens and reduce or prevent allergies.

This invention has been described herein in considerable detail to provide those skilled in the art with information relevant to apply the novel principles and to construct and use such specialized components as are required. However, it is to be understood that the invention can be carried out by different equipment, materials and devices, and that various modifications, both as to the equipment and operating procedures, can be accomplished without departing from the scope of the invention itself. As such, these changes and modifications are properly, equitably, and intended to be, within the full range of equivalence of the following claims.

We claim:

1. A method of sanitizing food contact surfaces comprising:
   a. applying a liquid composition at pH 6 to 7.5 comprising 40 to 80 ppm of an allergen deactivating agent selected from the group consisting of a hypohalous acid, a hypohalous acid salt, and a combination thereof to a food contact surface; and
   b. sanitizing the surface with respect to bacteria selected from the group consisting of *Staphylococcus aureus, Salmonella, E.coli*, and combinations thereof; and
   wherein the food contact surface is a kitchen surface.

2. A method of sanitizing food contact surfaces comprising:
   a. applying a liquid composition at pH 6 to 7.5 comprising 40 to 80 ppm of an allergen deactivating agent selected from the group consisting of a hypohalous acid, a hypohalous acid salt, and a combination thereof to a food contact surface; and
   b. sanitizing the surface with respect to bacteria selected from the group consisting of *Staphylococcus aureus, Salmonella, E.coli*, and combinations thereof; and
   wherein the food contact surface is a counter top.

* * * * *